(12) United States Patent
Chaturvedi et al.

(10) Patent No.: US 11,518,733 B2
(45) Date of Patent: Dec. 6, 2022

(54) PROCESS FOR PREPARATION OF HIGHLY PURE FINGOLIMOD HYDROCHLORIDE

(71) Applicants: Akshay Kant Chaturvedi, Bhiwadi (IN); Vimal Kumar Shrawat, Bhiwadi (IN); Sahdev Singh, Bhiwadi (IN)

(72) Inventors: Akshay Kant Chaturvedi, Bhiwadi (IN); Vimal Kumar Shrawat, Bhiwadi (IN); Sahdev Singh, Bhiwadi (IN)

(73) Assignee: SHIVALIK RASAYAN LIMITED, Rajasthan (IN)

( * ) Notice: Subject to any disclaimer, the term of this patent is extended or adjusted under 35 U.S.C. 154(b) by 21 days.

(21) Appl. No.: 17/468,722

(22) Filed: Sep. 8, 2021

(65) Prior Publication Data

US 2022/0064102 A1    Mar. 3, 2022

(51) Int. Cl.
*C07C 213/02* (2006.01)
*C07C 213/10* (2006.01)
*C07C 231/12* (2006.01)

(52) U.S. Cl.
CPC .......... *C07C 213/02* (2013.01); *C07C 213/10* (2013.01)

(58) Field of Classification Search
CPC .... C07C 213/02; C07C 213/10; C07C 231/12
See application file for complete search history.

(56) References Cited

U.S. PATENT DOCUMENTS

| | | |
|---|---|---|
| 5,604,229 A | 2/1997 | Fujita et al. |
| 5,747,498 A | 5/1998 | Schnur et al. |
| 8,440,823 B2 | 5/2013 | Murugesan et al. |
| 8,735,627 B2 | 5/2014 | Marom et al. |
| 8,952,022 B2 | 2/2015 | Gore et al. |
| 9,056,813 B2 | 6/2015 | Gharpure et al. |
| 9,216,943 B2 | 12/2015 | Katkam et al. |
| 9,428,468 B2 | 8/2016 | Baratella et al. |
| 9,643,914 B2 | 5/2017 | Gurjar et al. |
| 9,732,030 B2 | 8/2017 | Shrawat et al. |
| 9,815,772 B2 | 11/2017 | Kumar et al. |

FOREIGN PATENT DOCUMENTS

| | | |
|---|---|---|
| WO | 2012041359 A1 | 4/2012 |
| WO | 2013156835 A1 | 10/2013 |
| WO | 2014111949 A1 | 7/2014 |
| WO | 2015023170 A1 | 2/2015 |

*Primary Examiner* — Sikarl A Witherspoon

(57) ABSTRACT

The present invention provides process for preparation of highly pure Fingolimod hydrochloride (I),

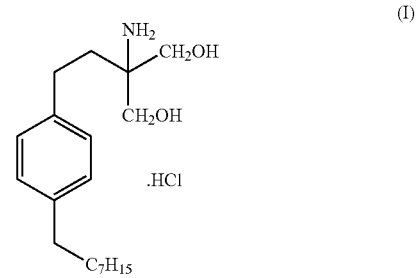

without involving the use of column chromatographic purification in the entire process. Fingolimod hydrochloride (I) obtained by the process of present invention may be useful as active pharmaceutical ingredient in pharmaceutical compositions for the treatment of autoimmune related disorder including multiple sclerosis.

8 Claims, 3 Drawing Sheets

PROCESS FOR PREPARATION OF HIGHLY PURE FINGOLIMOD HYDROCHLORIDE

FIELD OF THE INVENTION

The present invention relates to process of preparation of highly pure Fingolimod hydrochloride.

The process of present invention is an improvement over prior disclosed processes by without involving the use of column chromatographic purification in the entire process.

BACKGROUND OF THE INVENTION

Fingolimod hydrochloride (FTY720) has the IUPAC name as 2-amino-2-[2-(4-octylphenyl) ethyl] propane-1,3-diol hydrochloride and has the following structure:

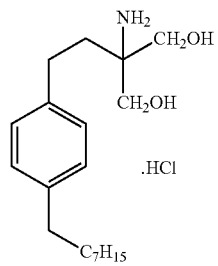

Fingolimod hydrochloride is currently available as GILE-NYA. It has been found to be useful in the treatment or prevention of various autoimmune conditions and with the patients having the relapsing forms of multiple sclerosis.

Fujita et al. U.S. Pat. No. 5,604,229 is the first disclosure of the Fingolimod, its processes and other related compounds. Patent discloses 2-Amino-1, 3-propanediol compounds of the formula (I)

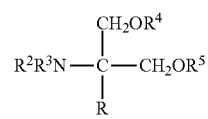

wherein R is an optionally substituted straight or branched carbon chain, an optionally substituted aryl, an optionally substituted cycloalkyl or the like, and $R^2$, $R^3$, $R^4$ and $R^5$ are the same or different and each is a hydrogen, an alkyl, an aralkyl, an acyl or an alkoxycarbonyl, pharmaceutically acceptable salts thereof and immune suppressants comprising these compounds as active ingredients. The 2-amino-1, 3-propanediol compounds disclosed immunosuppressive action and are useful for suppressing rejection in organ or bone marrow transplantation, prevention and treatment of autoimmune diseases or as reagents for use in medicinal and pharmaceutical fields.

Krajcovic et al in WO2012041359 discloses the process of preparing Fingolimod and its acid addition salt as per Scheme-1.

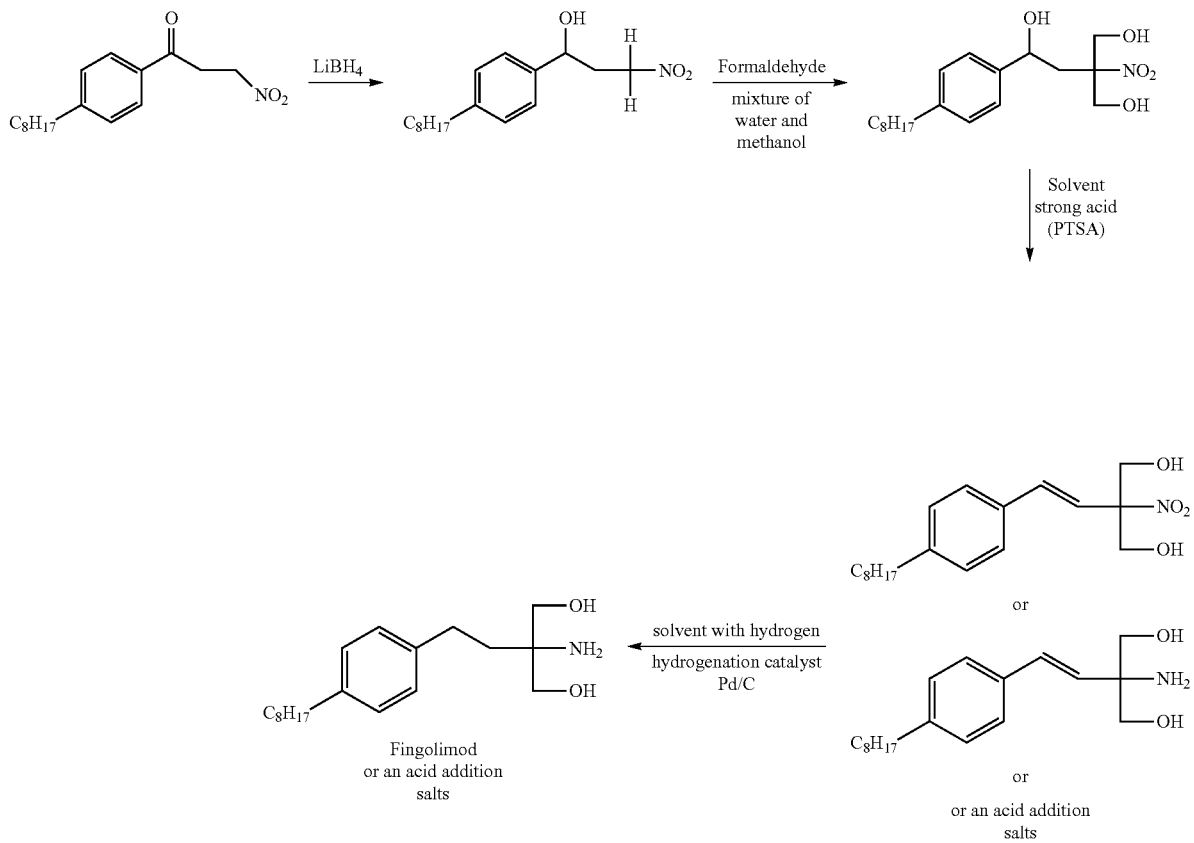

Kothakonda et al in U.S. Pat. No. 8,735,627 discloses a process for preparation of Fingolimod according to the below mentioned Scheme-2.

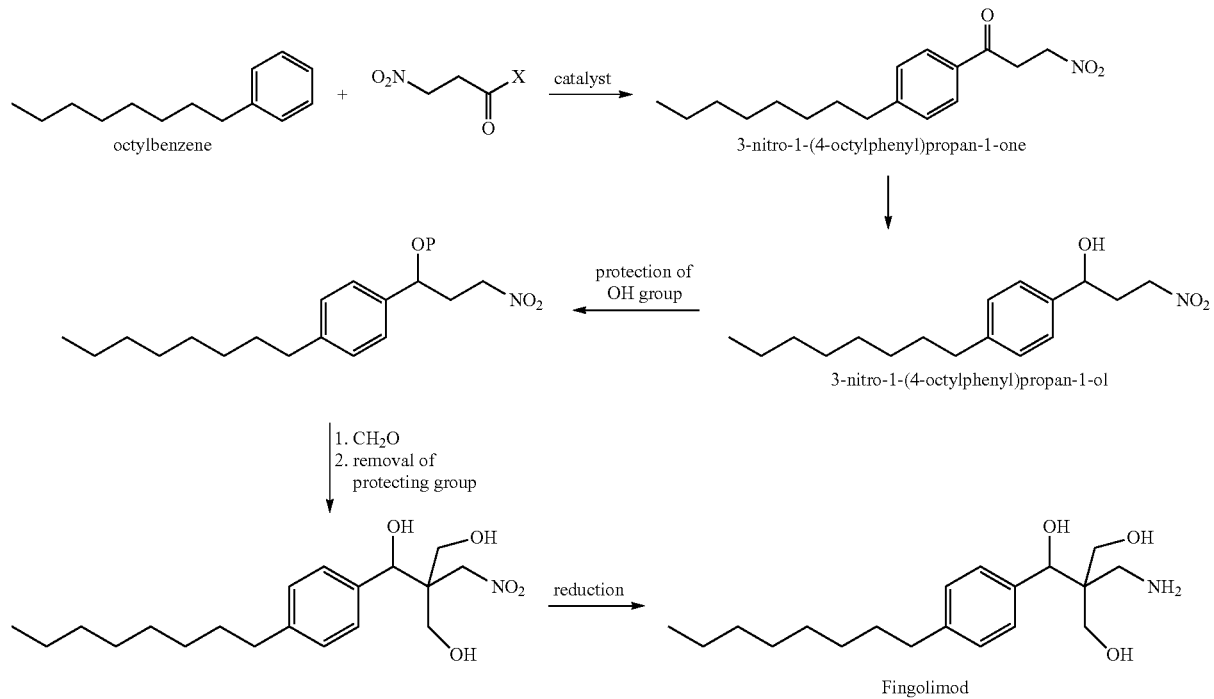

wherein
X = Halogen or anhydride
Catalyst = Friedel-craft catalyst
P = Protecting group Katkam et al. in U.S. Pat. No. 9,216,943 discloses a process for preparation of Fingolimod hydrochloride which involves the reaction steps as depicted in the below mentioned Scheme-3:

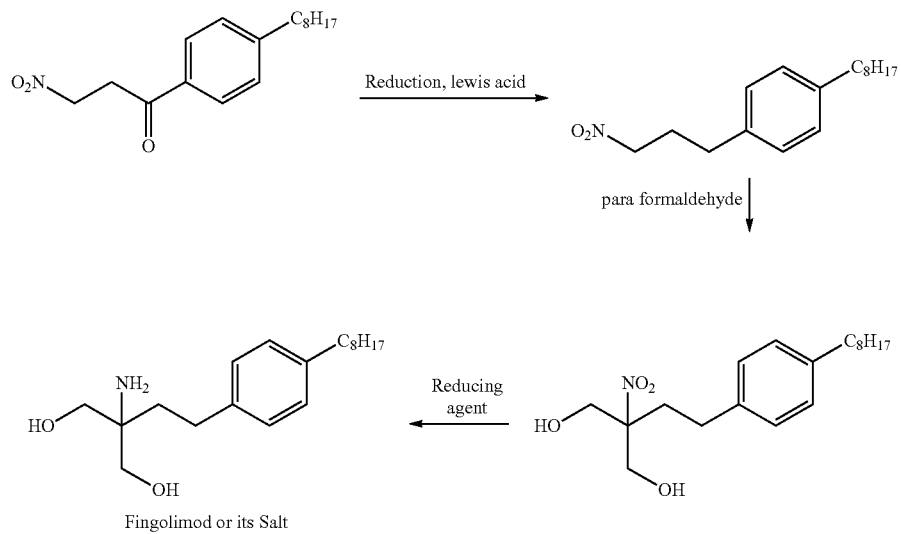

Gharpure et al. in U.S. Pat. No. 9,056,813 discloses a process for preparation of Fingolimod containing the regioisomeric impurity (Ib), wherein the disclosed method follows the multi-step process to eliminate the regioisomeric impurity from the Fingolimod free base and its hydrochloride.
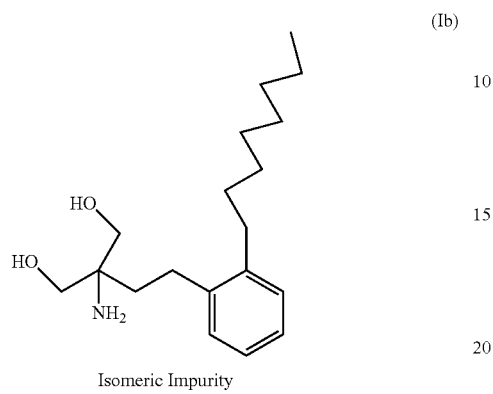
Isomeric Impurity
Reaction Scheme-4 is as follows:
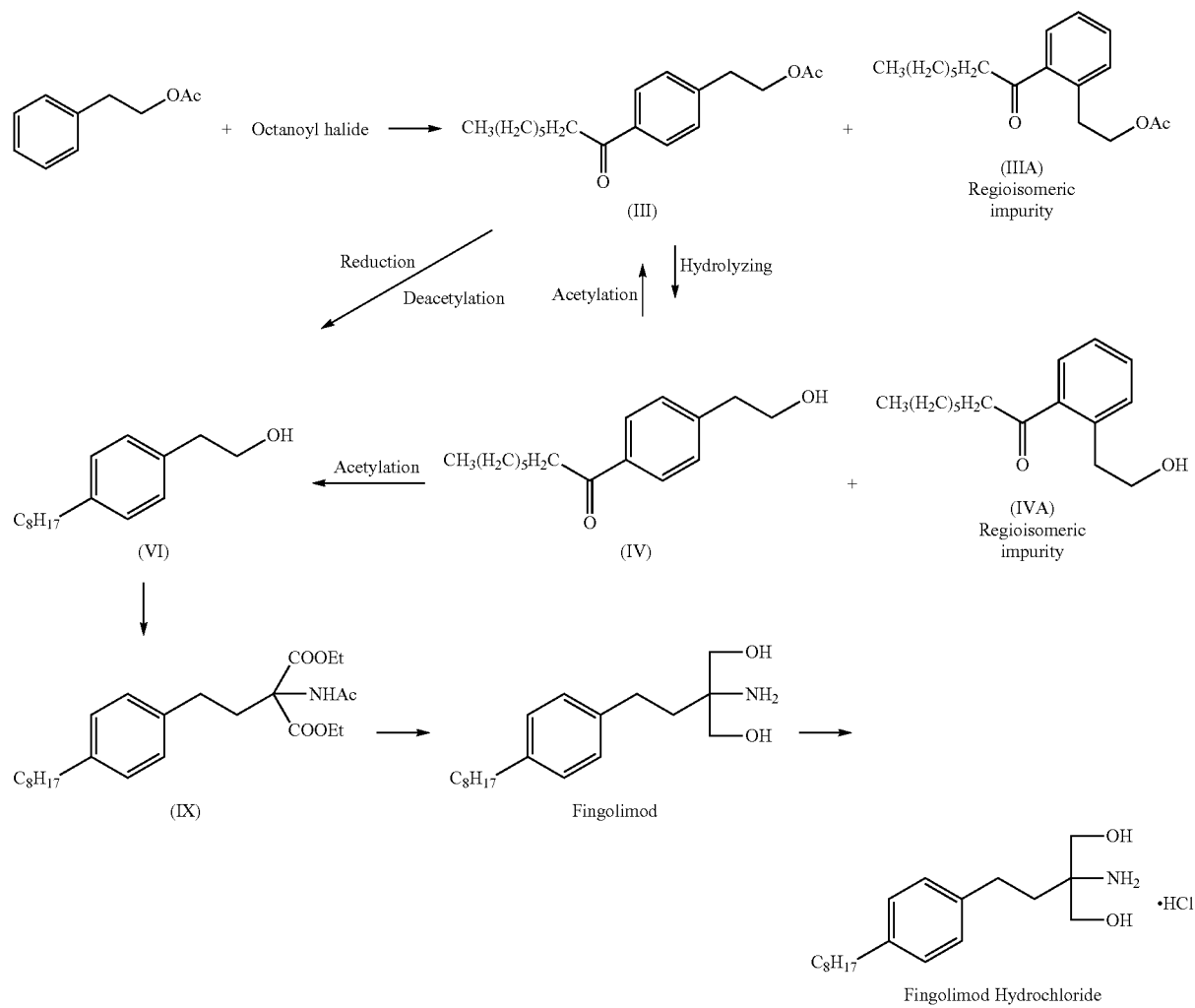

Konakanchi et al in PCT application WO2014111949 discloses the intermediates and process for the preparation of high purity Fingolimod hydrochloride according to the Scheme-5.
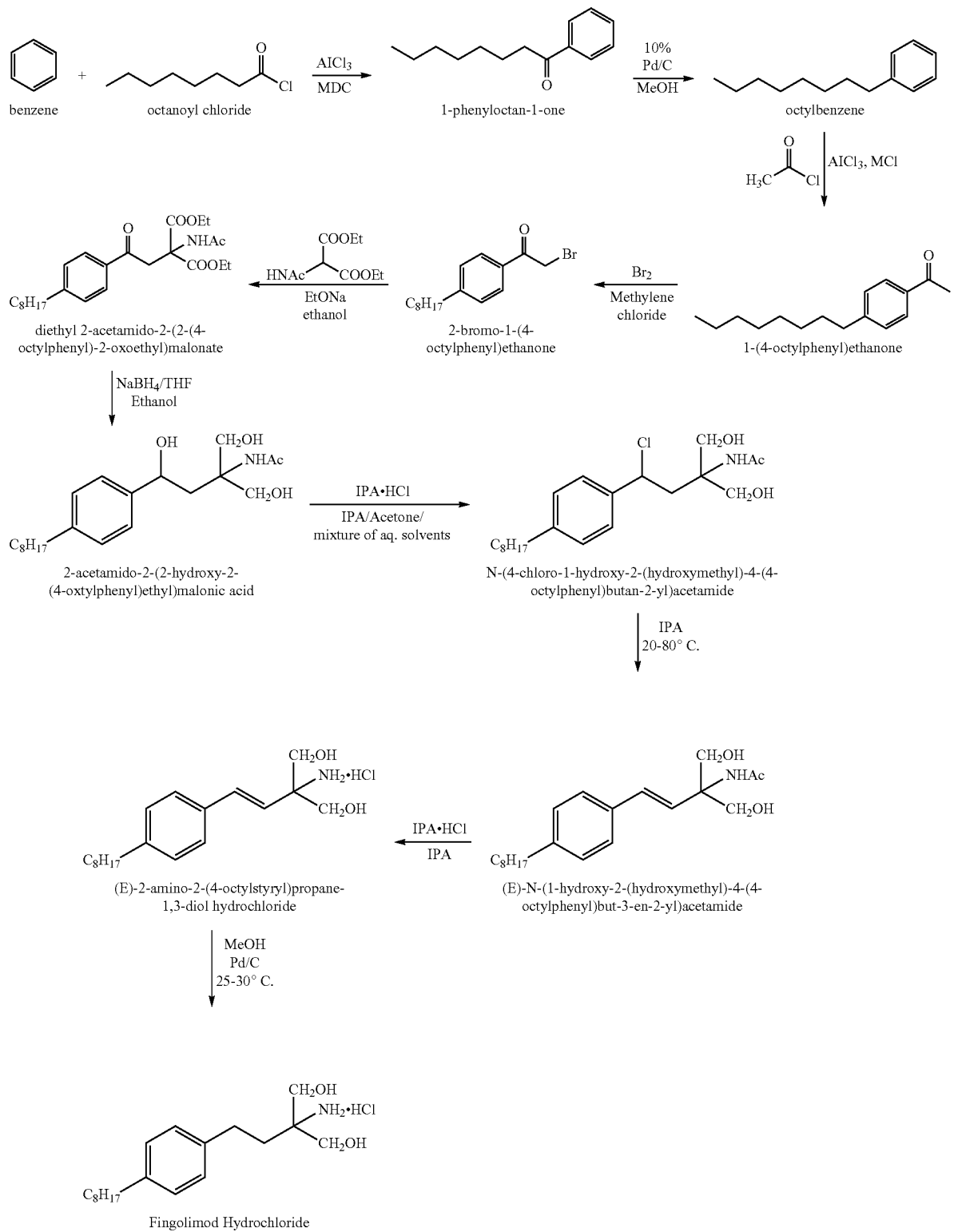
Scheme-5: Process as per WO2014111949

Kothakonda et al in U.S. Pat. No. 9,815,772 discloses the preparation method of Fingolimod hydrochloride by the following Scheme-6:

was used for the step-2 reduction whereby the step-2 product obtained had purity of about 90% (by HPLC). This material was 2 times purified by

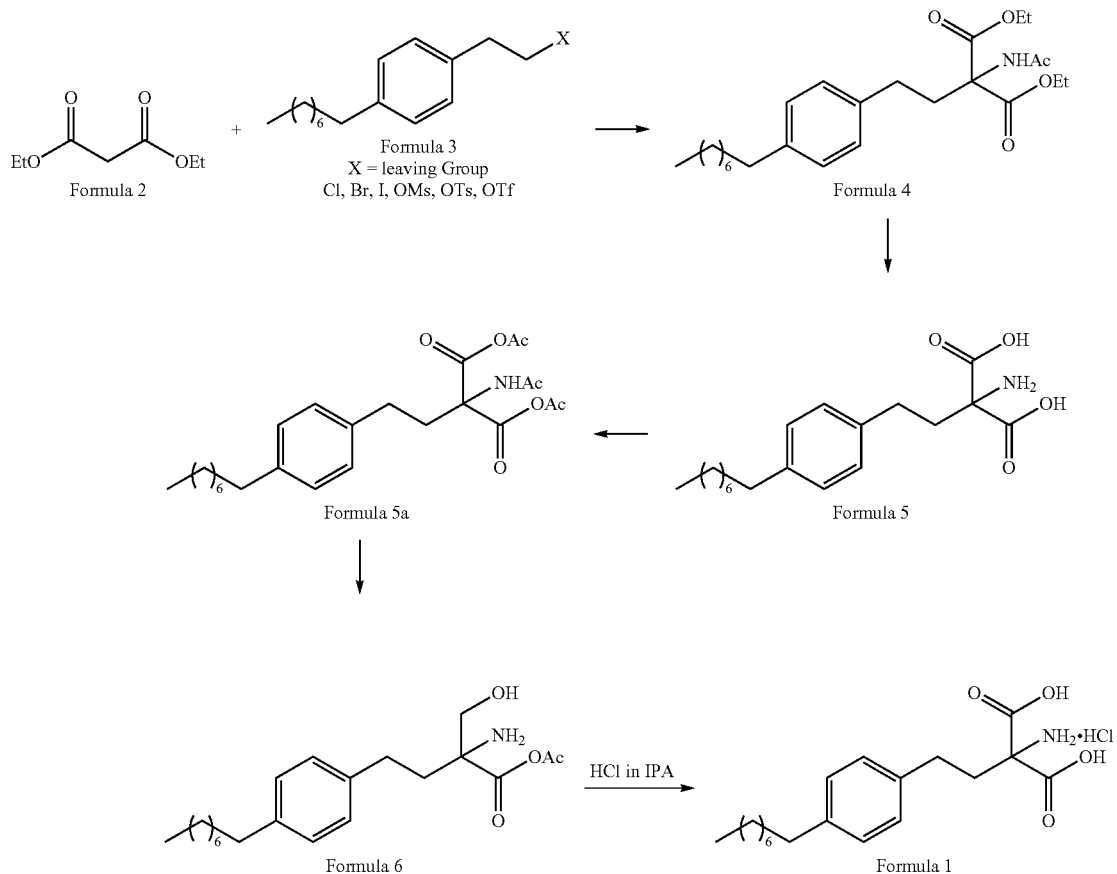

Scheme-6: Process as per US9815772

Disclosed scheme is a multistep process which is difficult to handle in the large scale manufacturing in the industries.

Shrawat et al in U.S. Pat. No. 9,732,030 discloses the process of preparation of Fingolimod base and its hydrochloride salt. More particularly in the step 1 of example 1, on reproducing entity resulted in a desired regioisomer ratio of not exceeding 55-70% (by HPLC) (pls. refer—FIG. 1), whereby the residue obtained was subjecting to purify by column chromatography over silica gel (230-400 mesh) using an eluent system of ethyl acetate and hexane. The column purified material was still having purity of not exceeding of 72-80%. Said material dissolving in methanol and recrystallised by low temperature to get a purity of >99.5%.

The disadvantage of the process is that it was observed the process is very tedious, cumbersome and time consuming method and has several repeated purification.

Mukund K. et al. in U.S. Pat. No. 9,643,914 discloses the preparation method of Fingolimod hydrochloride by the following scheme:

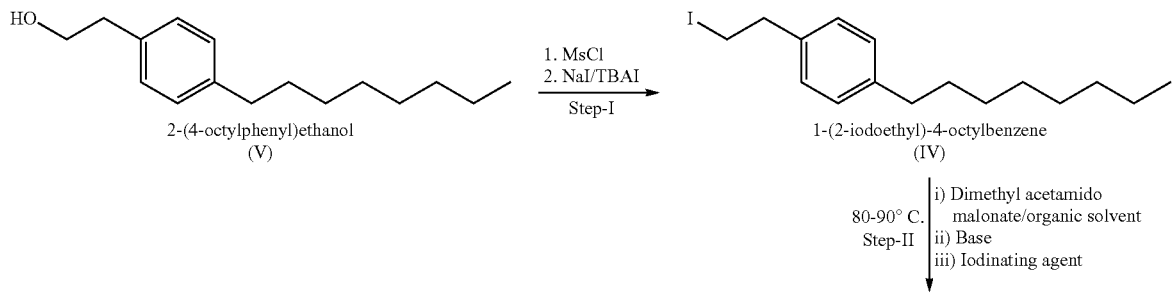

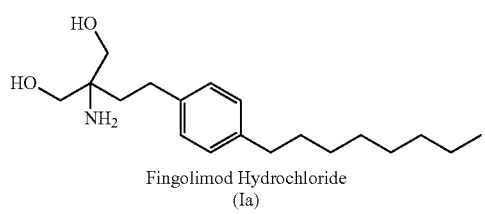

Fingolimod Hydrochloride
(Ia)

1. Reduction/Hydrolysis
2. HCl-Solvent
3. Purification

Step-III

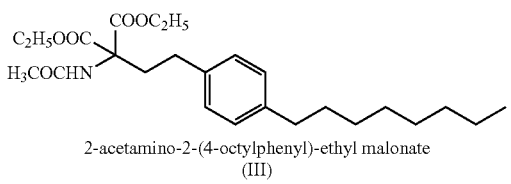

2-acetamino-2-(4-octylphenyl)-ethyl malonate
(III)

Further, in view of the existence of various literature/information known for processes related to preparation of Fingolimod hydrochloride, there exists a need of process/es, which are not only industrially and economically feasible process but also amenable to scale up and provide improved yields & quality.

Thus, the inventors of the present application provide a simple and industrially viable process for the preparation of Fingolimod or its hydrochloride without involving the use of column chromatographic purification in the entire process.

SUMMARY OF INVENTION

Particular aspects of the present application relate to the process/es for preparation of Fingolimod and its salts. The application further relates to processes for preparation of Fingolimod HCl (I) which is substantially free from process related impurities. Fingolimod HCl (I) obtained by the process according to the present invention is useful as active pharmaceutical ingredient in pharmaceutical compositions for the treatment of autoimmune related disorders including multiple sclerosis. Different aspects of the present application are summarized herein below individually.

In one aspect of the present application, the present invention relates to a process for preparation of highly pure Fingolimod hydrochloride (I)

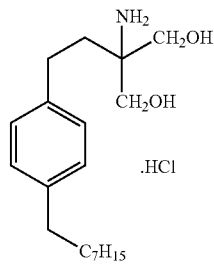

(I)

comprising the steps of:

a). selectively octanoylating the compound of formula (A) at temperature ranging between −10 to −20° C. in the presence of a lewis acid and an organic solvent to get para substituted enriched regioisomer.

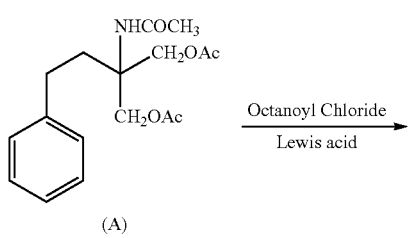

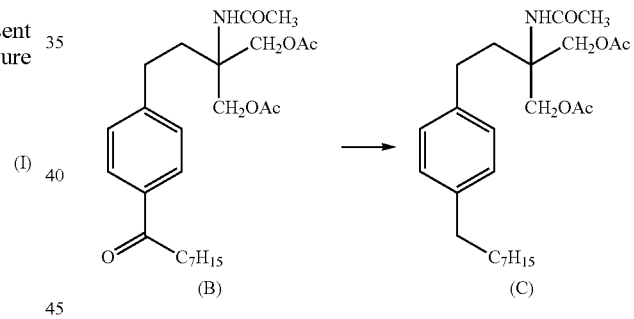

b). purifying the compound of formula (B) without involving the column chromatography.

c). performing hydrogenation selectively of step a) compound of formula (B) to obtain the compound of formula (C).

d). reacting the compound of formula (C) in the presence of alkali hydroxide and an organic solvent to get Fingolimod free base.

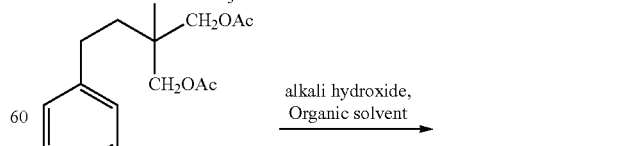

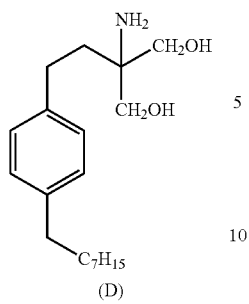

(D)

e). converting Fingolimod free base (D) into Fingolimod hydrochloride (I) in an organic solvent.

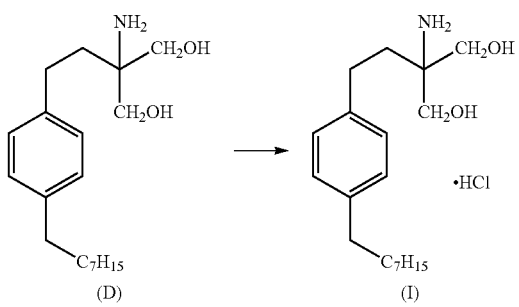

(D) → (I)

In another aspect of the present invention, it relates to the process for purification of compound of formula (B) comprising the steps of:
a) extracted the compound of formula (B) in an organic solvent
b) dried the organic layer
c) recover the organic solvent
d) crystallisation using hydrocarbon solvent
e) isolating the desired enriched para substituted regioisomer is in the range of 70-90%.

In yet another aspect according to the present invention it relates to highly pure Fingolimod hydrochloride having purity exceeding 99.8% (by HPLC).

DETAILED DESCRIPTION

Figure 1:
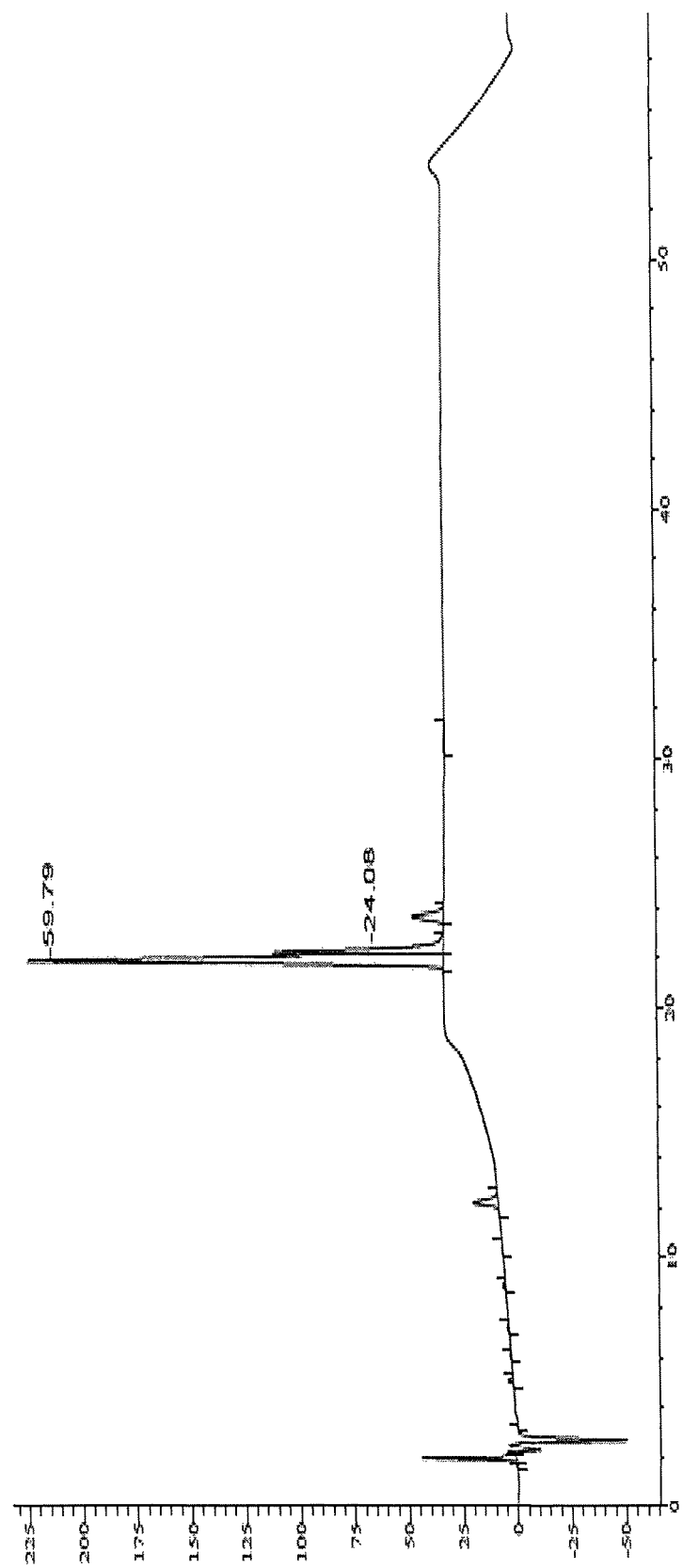
FIG. 01 is an illustration of HPLC graph of compound of formula (B) after reproducing prior process of U.S. Pat. No. 9,732,030
Figure 2:
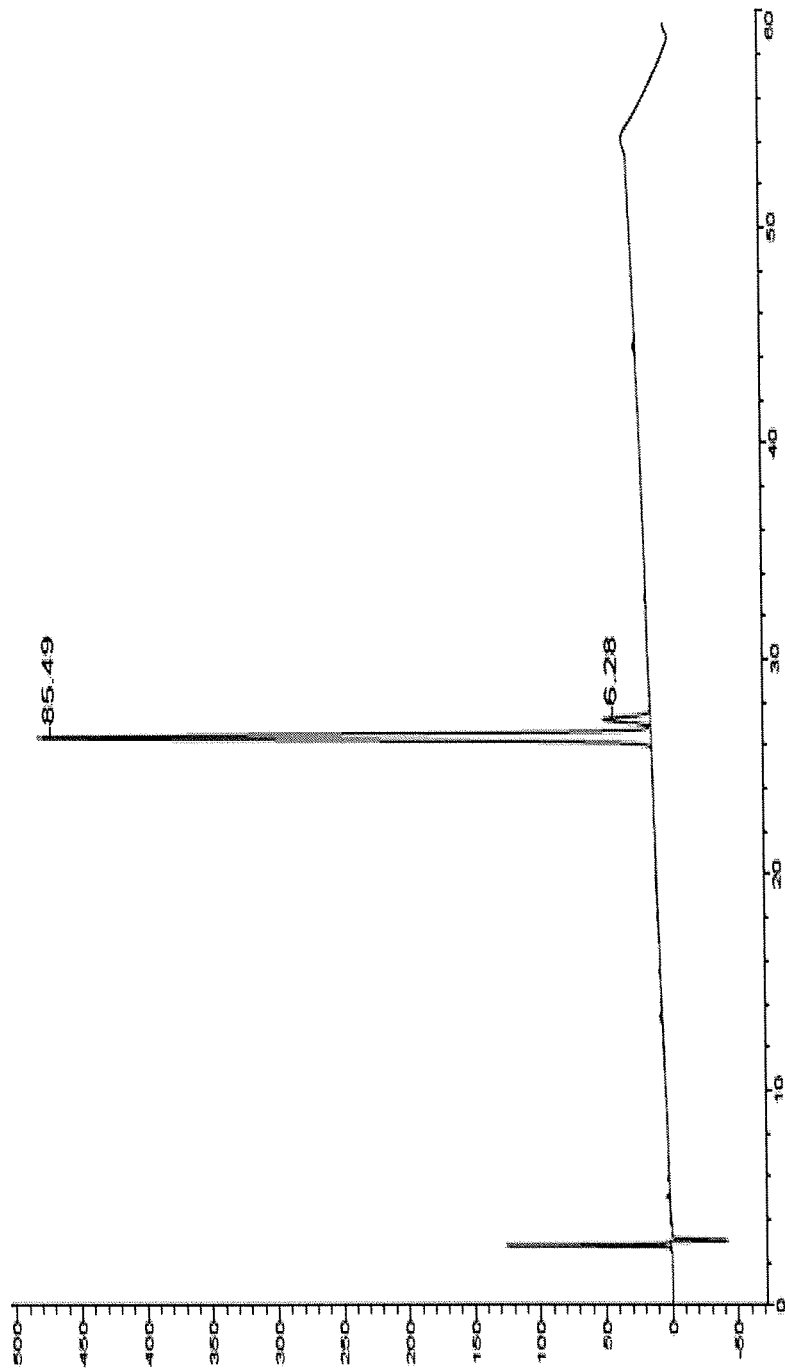
FIG. 02 is an illustration of HPLC graph of compound of formula (B) prepared according to step 1 of the Example.

As set forth herein, embodiments of the present invention relate to a process for preparation of Fingolimod HCl (I). The present invention deals with a simple and industrially efficient process for making the compound of formula (B), which exhibits various advantages over other ways of conversion of compound (A) to the compound (B) known in the art. The advantages are discussed on the relevant places of further description. Individual embodiments of the present invention are detailed herein below separately.

In one embodiment of the present application, it provides a process for preparing Fingolimod HCl (I).

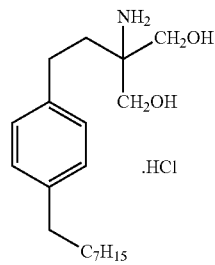

(I)

In a further embodiment, the present application, it provides Fingolimod or a pharmaceutically acceptable salt free of undesired regioisomeric impurity.

In an embodiment of the present application, it provides a process for preparation of Fingolimod hydrochloride (I), comprising the steps of:
a). selectively octanoylating the compound of formula (A) at temperature ranging between −10 to −20° C. in the presence of a lewis acid and an organic solvent to get para substituted enriched regioisomer.

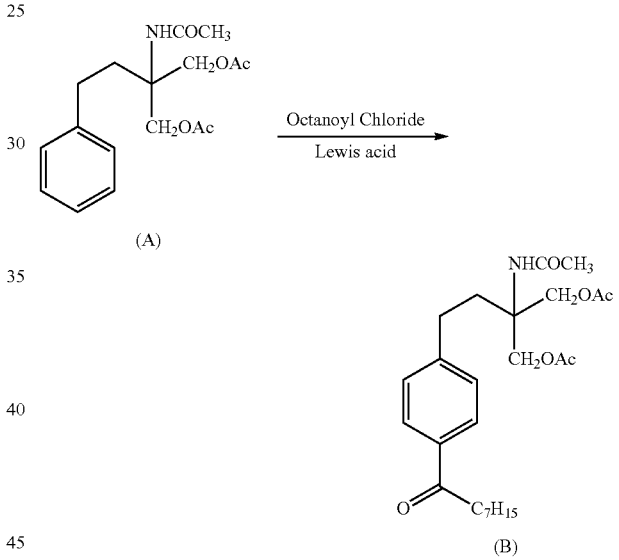

b). purifying the compound of formula (B) without involving the column chromatography.
c). performing hydrogenation selectively of step a) compound of formula (B) to obtain the compound of formula (C).

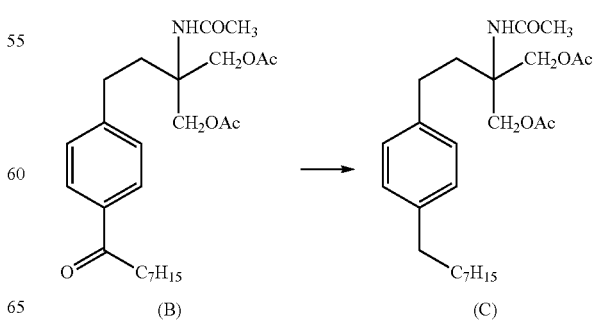

(B) → (C)

d). reacting the compound of formula (C) in the presence of alkali hydroxide and an organic solvent to get Fingolimod free base.

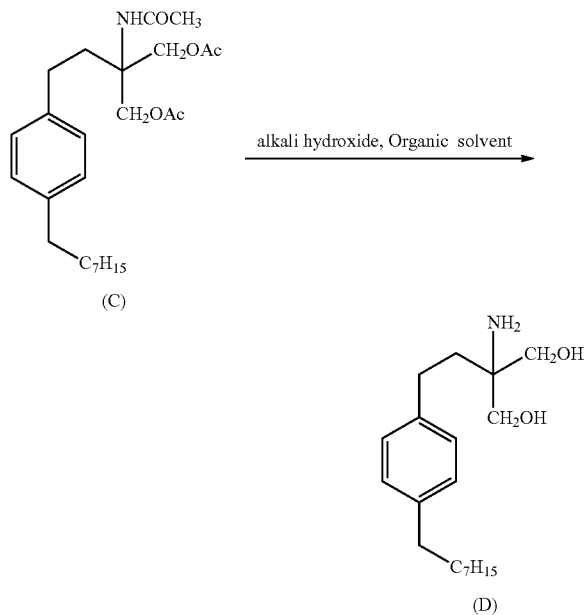

e). converting Fingolimod free base (D) into Fingolimod Hydrochloride (I) in an organic solvent.

The individual steps of the process according to the present invention for preparing Fingolimod Hydrochloride (I) are detailed separately herein below.

Step a) process comprises reacting 2-acetamido-2-(4-octanoylphenethyl) propane-1, 3-diyl diacetate (A) with octanoyl chloride and in the presence of Lewis acid and halohydrocarbon in an inert atmosphere to form 2-acetamido-2-(4-octylphenethyl) propane-1, 3-diyl diacetate (B).

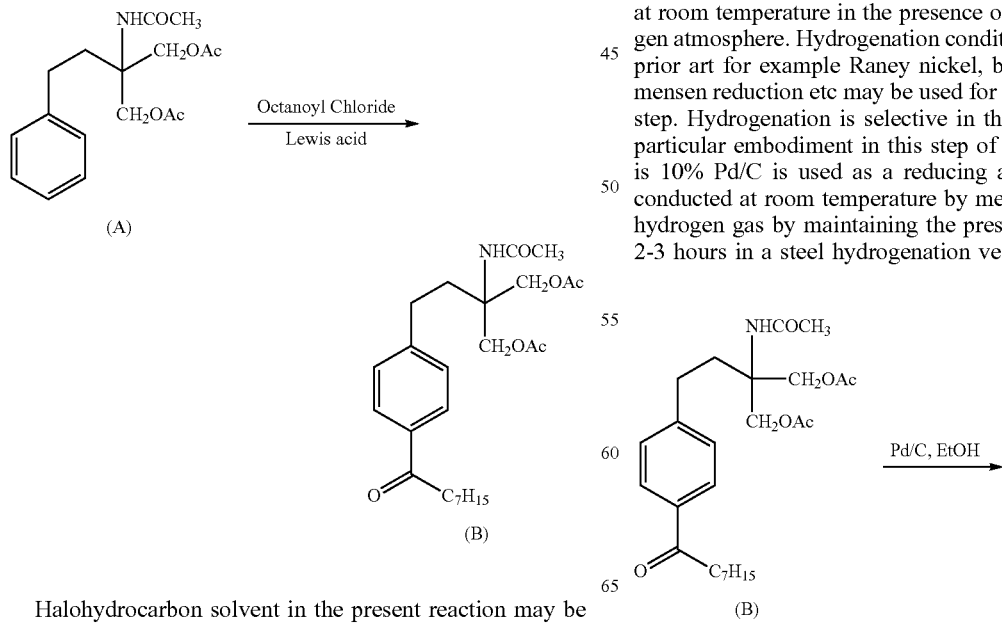

Halohydrocarbon solvent in the present reaction may be selected from dichloromethane, dichloroethane or chloroform. Lewis acid which is a commonly known Friedal-Craft's catalyst may further be selected from $FeCl_3$, $AlCl_3$, $TiCl_4$, $ZnCl_2$ or $BF_3$.

Inert atmosphere to be utilized for the conduct of the present reaction may be suitably chosen by a person skilled in the art, according to the methods provided in literature. For e.g. a non-limiting illustration of inert atmosphere can be nitrogen atmosphere.

Addition of the compound of formula (A) to a solution of octanoyl chloride in halohydrocarbon solvent in the presence of a Friedal-Craft catalyst is done at a temperature ranging between −10° C. to −15° C. However, a most suitable range of temperature observed by the inventors of the present invention was found to be in the range of −12° C. to −14° C. for getting the optimum quality of the product with desired purity and yield of the compound of formula (B).

Step b) a process for purifying the compound of formula (B) comprising the steps of:

a) extracted the compound of formula (B) in an organic solvent
b) dried the organic layer
c) recover the organic solvent
d) crystallisation using hydrocarbon solvent
e) isolating the desired enriched para substituted regioisomer is in the range of 70-90%.

2-acetamido-2-(4-octylphenethyl) propane-1, 3-diyl diacetate (B) the product of this step a is purified without involving the column chromatography and performed the extraction by using an organic solvent which may be further selected from dichloromethane, dichloroethane or chloroform followed by dried the organic layer with anhydrous sodium sulfate and recovered the solvent by distillation. In the obtained residue added hydrocarbon solvent preferably hexane to achieve the desired enriched para substituted regioisomer is in the range of 70-90%.

Step c) process comprising the hydrogenation of the compound of formula (B) to get compound of formula (C) at room temperature in the presence of ethanol under nitrogen atmosphere. Hydrogenation conditions are known in the prior art for example Raney nickel, birch reduction, clemmensen reduction etc may be used for the conversion of this step. Hydrogenation is selective in this step. In one of the particular embodiment in this step of the present invention is 10% Pd/C is used as a reducing agent. Hydrogenation conducted at room temperature by means of purging of the hydrogen gas by maintaining the pressure of 4 Kg/cm² for 2-3 hours in a steel hydrogenation vessel (autoclave).

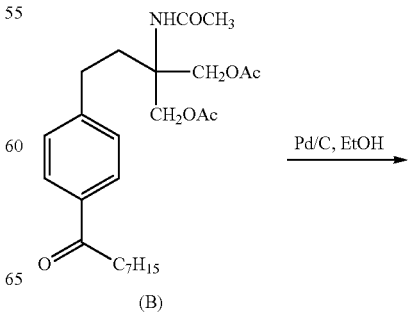

-continued

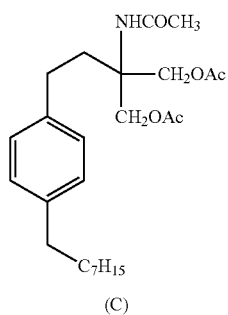

(C)

Step d) process comprising the treatment of 2-acetamido-2-(4-octylphenethyl) propane-1, 3-diyl diacetate (C) with a base and an organic solvent to get the Fingolimod free base (D).

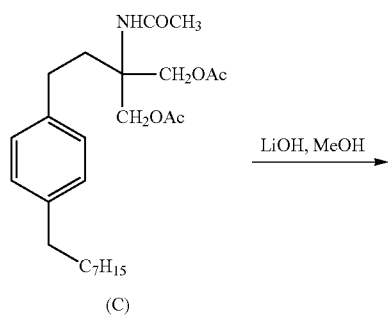

Base used in this step of the present invention more particularly is an Alkali metal hydroxide. Alkali metal hydroxide may be selected from LiOH, NaOH, KOH or may optionally be used in the form of a solution in water or its hydrate form.

More preferably the organic solvent used in this step of the present invention is alcohol containing 1-4 carbon atoms and the alcoholic solvent may be selected from the group consisting of methanol, ethanol, isopropanol or mixtures thereof.

In an another embodiment according to the present invention the reaction is conducted at reflux temperature by the slow addition of the base (LiOH) in the reaction mixture of 2-acetamido-2-(4-octylphenethyl) propane-1, 3-diyl diacetate (C) and alcohol (methanol) for 2-3 hours.

Fingolimod free base product of this step of the present invention may be extracted (twice) from the reaction mixture by using a suitable organic solvent like ethyl acetate. Excess amount of the ethyl acetate can be removed from the Fingolimod free base by drying under vacuum at 45° C. for 6-7 hours.

Step e) In one embodiment, the present invention provides a process for preparing Fingolimod hydrochloride by the addition of the Fingolimod free base and ethyl acetate at room temperature followed by increasing the temperature up to refluxing temperature (~70° C.).

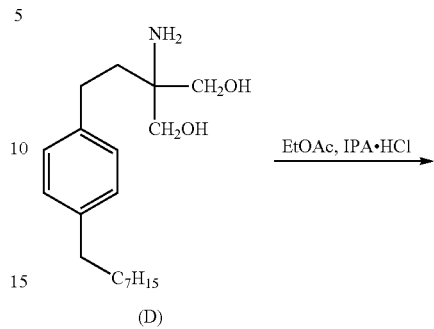

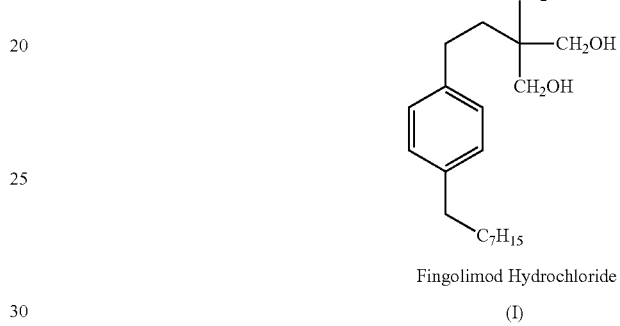

The Fingolimod free base obtained in step d can be converted to a suitable pharmaceutically acceptable acid addition salt, wherein acid can be an organic acid like $CH_3COOH$, fumaric acid, $CH_3COOSO_3H$ or $C_6H_5SO_3H$ or inorganic acid like hydrochloric acid, hydrobromic acid or sulfuric acid.

The reaction of Fingolimod free base with hydrochloric acid may be carried out in an alcoholic solvent.

In one embodiment according to the present invention the Fingolimod is converted to its hydrochloride salt by treatment with hydrochloric acid in isopropanol.

Desired product in this step of the present invention washed with ethyl acetate and the excess amount of the ethyl acetate can be removed from the Fingolimod hydrochloride by drying under vacuum at 45° C. for 6-7 hours.

Figure 3:
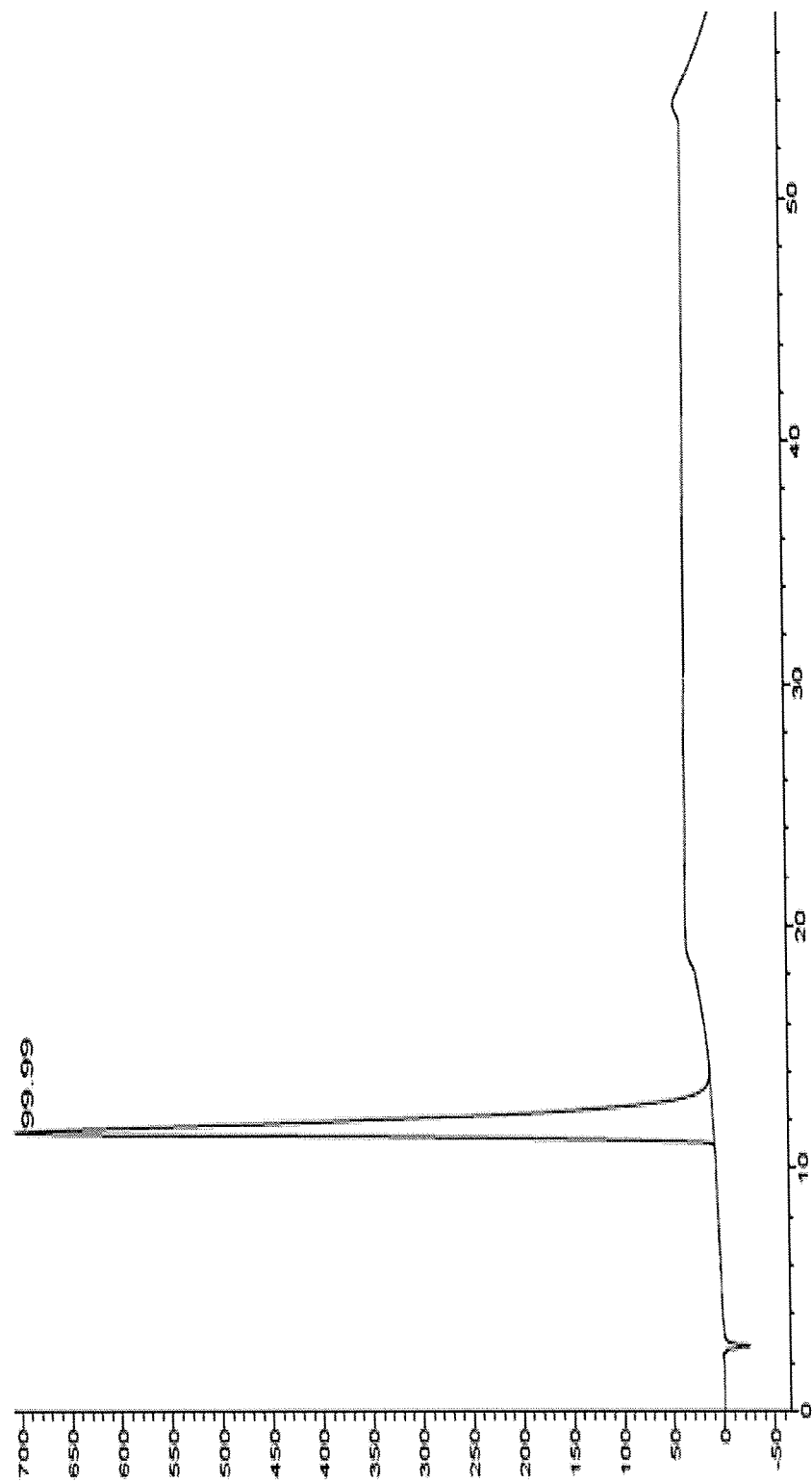
FIG. 03 is an illustration of HPLC graph of Fingolimod hydrochloride prepared according to step 4 of the Example.

In an embodiment according to the present invention, it provides a process for preparation of Fingolimod hydrochloride (I), having purity of greater than 99.8% characterized by HPLC pattern as per FIG. 3.

The final product obtained is characterized by HPLC substantially according to FIG. 3, thereby confirming that the Fingolimod hydrochloride obtained as final end product is Fingolimod hydrochloride (I).

In yet another embodiment according to the present invention, it provides Fingolimod or a pharmaceutically acceptable salt free of regioisomeric impurity or its salt thereof below detection limit (BDL) as determined by HPLC.

In yet further embodiment according to the present invention it relates to highly pure Fingolimod hydrochloride having purity exceeding 99.8% (by HPLC).

In still another embodiment according to the present invention, it provides Fingolimod or a pharmaceutically acceptable salt with content of regioisomeric impurity or its salt thereof, with purity data of at least 99.9% (FIG. 03) as determined by HPLC.

The product may be isolated from the reaction mass by conventional processes including filtering, washing and optional drying, which may be carried out under vacuum at 45° C. for 6-7 hours to retain the characteristic features of the product.

The merit of the process according to the present invention to provide the reproducibility of the desired para substituted enriched regioisomer is having the range of 75-89%. Regioisomeric impurities reduce the yield of the desired product and often form by-products that substantially increase the difficulty of isolating the desired product in high purity and yield. Here, in contrast, the present invention provides an efficient novel process for the preparation of fingolimod hydrochloride in order to obtain the desired para substituted enriched regioisomer in high purity and yield.

The process related impurities, including unreacted intermediates, side products, and other medium dependent impurities, that appear in the impurity profile of the Fingolimod hydrochloride can substantially be reduced by the process of the present invention resulting in the formation substantially pure.

In another embodiment, the final product Fingolimod HCl obtained by the processes of the present application may be formulated as solid compositions for oral administration in the form of capsules, tablets, pills, powders or granules useful in the treatment or prevention of autoimmune related disorder including multiple sclerosis. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin. The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising highly pure Fingolimod HCl obtained by the process of the present invention include, but are not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from highly pure Fingolimod HCl obtained by the process of the present invention may also comprise to include the pharmaceutically acceptable carrier used for the preparation of solid dispersion, wherever utilized in the desired dosage form preparation.

Certain specific aspects and embodiments of the present application will be explained in more detail with reference to the following example, which is provided by way of illustration only and should not be construed as limiting the scope of the invention in any manner.

EXAMPLE

The process for preparation of Fingolimod hydrochloride (I) according to the present invention is a multistep procedure which is detailed in the stepwise demonstration mentioned herein below:

Step 1) Preparation of
2-acetamido-2-(4-octanoylphenethyl) propane-1,
3-diyl diacetate

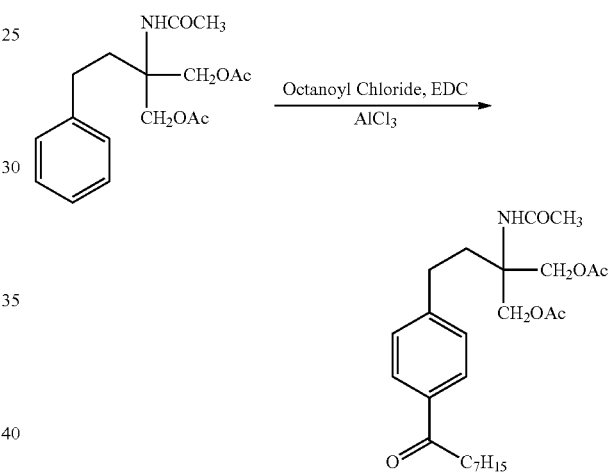

EDC (200 ml) was charged in a four necked RB flask and cooled up to −10° C. to −15° C., and under nitrogen atmosphere. Further Aluminium chloride (33.2 g) was added to the solution and stirred the reaction for 30 min. To this, octanoyl chloride (26.8 ml) was slowly added in an hour and the resulting reaction mixture stirred further for 1.5 hours, at −10° C. to −15° C. A solution of 2-acetamidol, 3-diacetoxy-2-(2-phenylethyl) propane (10 g dissolved in 40.0 ml EDC) was slowly added to the reaction mixture over a period of around 3 hours, maintaining the temperature between −10° C. to −15° C. The reaction mixture was then allowed to come to room temperature and stirred overnight for 16 hours. After completion of reaction as confirmed by HPLC, the reaction mixture was slowly poured into chilled water (200 ml) and stirred for 15-20 min. The EDC layer was separated and the aqueous layer was extracted with EDC (2×200 ml). The organic layers were combined, washed with saturated sodium chloride soln. (2×50 ml), dried over anhydrous sodium sulfate (10 g), filtered and concentrated under vacuum at temperature below 50° C. to get residue. To this added, Hexane (200 ml) and solution stirred for 2 h to give white solid. The solid material was filtered and suck dried for to afford 13.0 g title compound.

Purity (by HPLC): 85.49%; Yield: 93.34%

Step 2) Preparation of 2-acetamido-2-(4-octylphenethyl) propane-1, 3-diyl diacetate

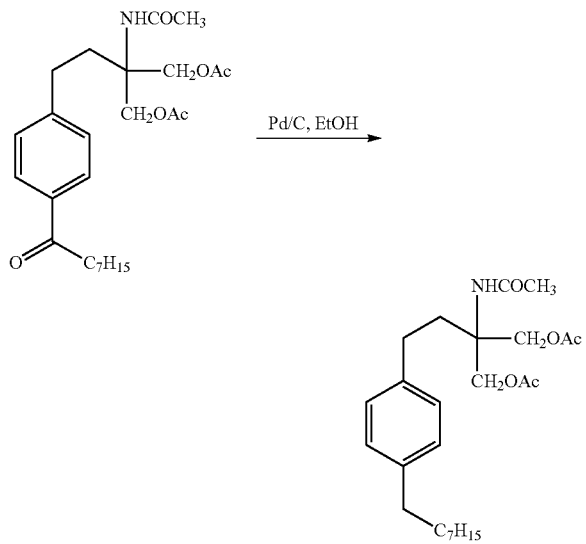

Charged 13 g of 2-acetamido-2-(4-octanoylphenethyl) propane-1, 3-diyl diacetate and ethanol (150 ml) in a 2 L steel hydrogenation vessel (autoclave), followed by addition of 10% Pd—C (2.73 g) under N₂ atmosphere. The reaction mixture was hydrogenated (4 kg/cm² H₂ pressure) at RT for 2-3 h. The progress of the reaction was confirmed by HPLC. After completion of the reaction, the reaction mixture was filtered through hyflo bed & washed with EtOH (20 ml). The filtrate was concentrated under reduced pressure below 50° C. to give 14.5 g of residue. Hexane (100 ml) was added to and stirred for 2-3 hours at RT. The separated white solid material was filtered to give 8.6 g crude 2-acetamido-2-(4-octylphenethyl) propane-1, 3-diyl diacetate compound (HPLC purity=97.25%). The obtained crude title compound was taken in methanol (105 ml) and stirred for 30 min at RT to get the clear solution. The solution was then cooled to 0-5° C. under stirring maintaining for two hours. The solid obtained was washed with chilled methanol, filtered and dried at 45° C. under vacuum for 2-3 hours, to obtain 6.3 g of title compound.

Purity (by HPLC): 99.17%; Yield: 48%

Step 3) Preparation of Fingolimod Free Base

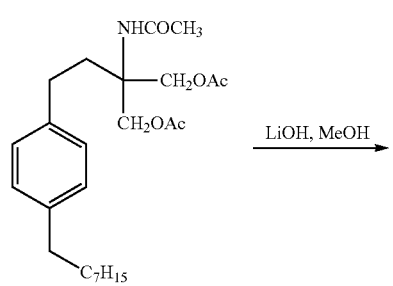

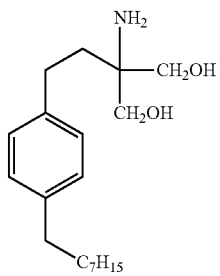

6 gm of 2-acetamido-2-(4-octylphenethyl) propane-1, 3-diyl diacetate was charged in a three necked RB flask, further added methanol (78 ml) and stirred at room temp till solution becomes clear. To this slowly added LiOH solution (12.2 g dissolved in 78 ml of DM Water) and then the reaction mixture stirred at reflux for 2-3 hours. The completion of reaction was monitored by HPLC. The reaction mixture was concentrated under reduced pressure below 45° C. to give residue which was taken in DM water (45 ml) and extracted twice with ethyl acetate (2×200 ml). The ethyl acetate layers were combined, washed with saturated brine (30 ml), dried over sodium sulfate (21 g) and concentrated under vacuum below 45° C. Ethyl acetate (12 ml) was added to residue and cooled the solution to 0-5° C., maintained the temperature for 2 hours and then filtered to give 3.6 g Fingolimod free base which was further dried under vacuum at 45° C. for 6-7 hours.

Purity (by HPLC): 99.92%; Yield: 93.34%

Step 4) Preparation of Fingolimod Hydrochloride

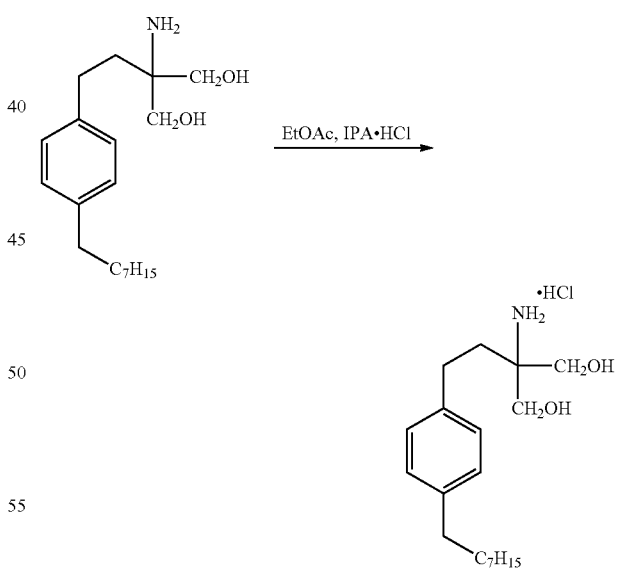

Fingolimod Hydrochloride

In a three necked round bottom flask Fingolimod free base (3.5 g) was charged to ethyl acetate (89 ml) and reaction stirred at room temperature for 15-20 min. The reaction mixture was slowly heated up to reflux (~70° C.) to get a clear solution. A mixture of 10% IPA-HCl (23 ml) was added to the reaction mixture at 50° C. over 10-15 min till pH 1-2 and resulting solution further stirred for 30 minutes. The reaction temperature was then cooled to 0-5° C. and maintained for 2-3 hours. The separated solid was filtered & washed with cold ethyl acetate to get the title compound. The material obtained was dried at 45° C. under full vacuum for 6-7 hours to get 3.4 g of Fingolimod hydrochloride.

Purity (by HPLC): 99.99%; Yield: 84.43%

While the present invention has been particularly described, persons skilled in the art will appreciate that many variations and modifications can be made. Therefore, the invention is not to be construed as restricted to the particularly described embodiments, examples and the scope and concept of the invention will be more readily understood by reference to the claims, which follow.

We claim:

1. A process for the preparation of highly pure Fingolimod hydrochloride (I) comprising the steps of:

a) selectively octanoylating the compound of formula (A) at temperature ranging between −12 to −20° C. in the presence of a Lewis acid and an organic solvent to get enriched para substituted regioisomer of the compound of formula (B);

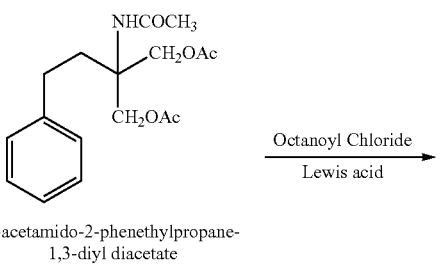

2-acetamido-2-phenethylpropane-1,3-diyl diacetate (A)

Octanoyl Chloride
Lewis acid

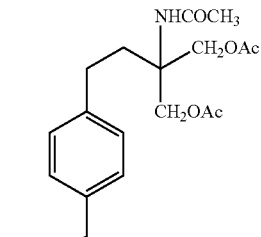

2-acetamido-2-(4-octanoylphenethyl) propane-1,3-diyl diacetate (B)

b) purifying the compound of formula (B) by using an organic solvent followed by recovering the solvent and crystallizing using hydrocarbon solvent to get the high purity para substituted regioisomer (B);

c) performing hydrogenation selectively of step b) compound of formula (B) to obtain the compound of formula (C);

2-acetamido-2-(4-octanoylphenethyl) propane-1,3-diyl diacetate (B)

2-acetamido-2-(4-octylphenethyl) propane-1,3-diyl diacetate (C)

d) reacting the compound of formula (C) in the presence of alkali hydroxide and an organic solvent to get compound of formula (D)

2-acetamido-2-(4-octylphenethyl) propane-1,3-diyl diacetate (C)

alkali hydroxide,
Organic solvent

N-(1-hydroxy-2-(hydroxymethyl)-4-(4-octylphenyl)butan-2-yl)acetamide (D)

e) hydro chlorinating the compound of formula (D) in an organic solvent to get highly pure Fingolimod hydrochloride (I)

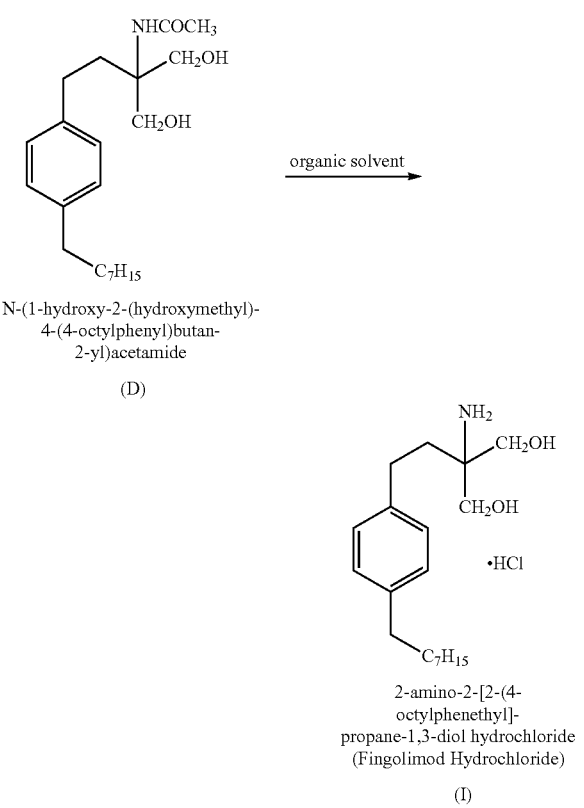

N-(1-hydroxy-2-(hydroxymethyl)-
4-(4-octylphenyl)butan-
2-yl)acetamide
(D)

2-amino-2-[2-(4-
octylphenethyl]-
propane-1,3-diol hydrochloride
(Fingolimod Hydrochloride)
(I)

2. The process as claimed in step a) of claim 1, the organic solvent used is selected from dichloromethane, dichloroethane or chloroform.

3. The process as claimed in step a) of claim 1, the temperature range to get the desired para substituted enriched regioisomer is −12° C. to −20° C.

4. The process of purifying as claimed in step b) of claim 1, the desired para substituted enriched regioisomer is obtained without using the column chromatography is having purity of 70-90%.

5. The process for preparing Fingolimod hydrochloride (1) according to step d) of claim 1, wherein organic solvent is selected from methanol, ethanol or isopropanol.

6. The process of purifying the enriched para substituted regioisomer of compound of formula (B)

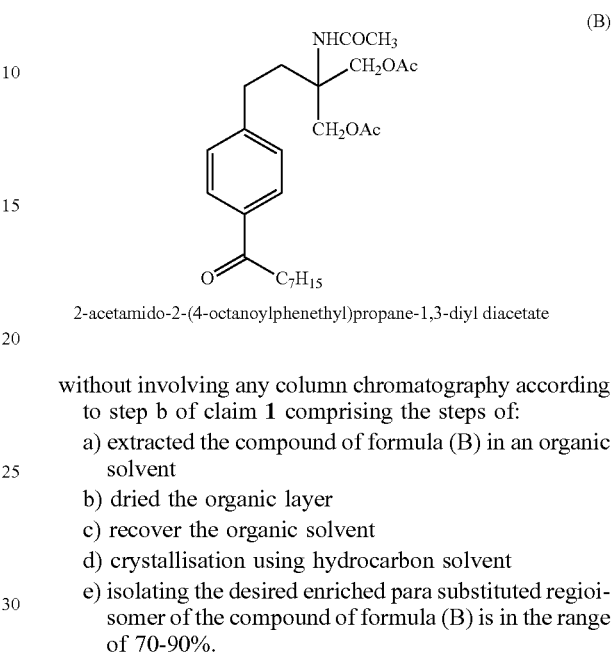

2-acetamido-2-(4-octanoylphenethyl)propane-1,3-diyl diacetate without involving any column chromatography according to step b of claim 1 comprising the steps of:
a) extracted the compound of formula (B) in an organic solvent
b) dried the organic layer
c) recover the organic solvent
d) crystallisation using hydrocarbon solvent
e) isolating the desired enriched para substituted regioisomer of the compound of formula (B) is in the range of 70-90%.

7. The process of purifying the enriched para substituted regioisomer of the compound of formula (B) of step a) according to claim 6, wherein organic solvent is selected from methylene dichloride, ethylene dichloride or chloroform and step d) hydrocarbon solvent is selected from hexane, n-heptane or cyclohexane.

8. A process of preparation of highly pure Fingolimod hydrochloride according to claim 1, is having purity of greater than 99.8% (by HPLC).

* * * * *